(12) United States Patent
Shaari

(10) Patent No.: US 9,125,907 B2
(45) Date of Patent: Sep. 8, 2015

(54) USE OF BOTULINUM NEUROTOXIN TO TREAT SUBSTANCE ADDICTIONS

(76) Inventor: Christopher Shaari, Demarest, NJ (US)

( * ) Notice: Subject to any disclaimer, the term of this patent is extended or adjusted under 35 U.S.C. 154(b) by 0 days.

(21) Appl. No.: 13/499,569

(22) PCT Filed: Sep. 30, 2010

(86) PCT No.: PCT/US2010/050822
§ 371 (c)(1),
(2), (4) Date: May 23, 2012

(87) PCT Pub. No.: WO2011/041483
PCT Pub. Date: Apr. 7, 2011

(65) Prior Publication Data
US 2012/0231034 A1    Sep. 13, 2012

Related U.S. Application Data

(60) Provisional application No. 61/247,278, filed on Sep. 30, 2009.

(51) Int. Cl.
*A61K 38/48* (2006.01)
*A61K 39/08* (2006.01)

(52) U.S. Cl.
CPC .................................. *A61K 38/4893* (2013.01)

(58) Field of Classification Search
CPC .......... A61K 38/48; A61K 9/00; A61K 45/06
USPC ........................................... 424/247.1, 239.1
See application file for complete search history.

(56) References Cited

U.S. PATENT DOCUMENTS

| | | | |
|---|---|---|---|
| 5,766,605 A * | 6/1998 | Sanders et al. ............. | 424/239.1 |
| 5,989,545 A | 11/1999 | Foster et al. | |
| 6,063,765 A | 5/2000 | Bennich et al. | |
| 6,365,164 B1 | 4/2002 | Schmidt | |
| 6,689,816 B2 | 2/2004 | Fogel | |
| 7,048,927 B2 * | 5/2006 | Brooks et al. ............. | 424/184.1 |
| 7,229,626 B2 * | 6/2007 | Donovan .................... | 424/247.1 |
| 7,390,496 B2 | 6/2008 | Ackerman | |
| 7,393,537 B2 | 7/2008 | Ackerman | |
| 7,393,538 B2 | 7/2008 | Ackerman | |
| 7,396,535 B2 | 7/2008 | Ackerman | |
| 7,422,753 B2 | 9/2008 | Ackerman | |
| 7,456,223 B2 | 11/2008 | Friedman | |
| 7,537,773 B1 | 5/2009 | Borodic | |
| 7,811,587 B2 * | 10/2010 | Donovan .................... | 424/247.1 |
| 8,008,457 B2 * | 8/2011 | Palma et al. ................ | 530/403 |
| 8,357,375 B2 * | 1/2013 | Palma et al. ................ | 424/194.1 |
| 8,470,337 B2 * | 6/2013 | Manack et al. ............ | 424/247.1 |
| 8,568,741 B2 * | 10/2013 | Mehdi ........................ | 424/239.1 |
| 2004/0059094 A1 * | 3/2004 | Bachmann et al. .......... | 530/350 |
| 2004/0213811 A1 | 10/2004 | Ackerman | |
| 2004/0213812 A1 | 10/2004 | Ackerman | |
| 2004/0213815 A1 | 10/2004 | Ackerman | |
| 2004/0253274 A1 * | 12/2004 | Voet ............................ | 424/239.1 |
| 2005/0147626 A1 * | 7/2005 | Blumenfeld ................ | 424/239.1 |
| 2005/0163809 A1 | 7/2005 | Kaji et al. | |
| 2005/0191320 A1 * | 9/2005 | Turkel et al. ................ | 424/239.1 |
| 2005/0196414 A1 * | 9/2005 | Dake et al. .................. | 424/239.1 |
| 2005/0196440 A1 * | 9/2005 | Masters et al. .............. | 424/464 |
| 2005/0261632 A1 * | 11/2005 | Xu ............................... | 604/173 |
| 2005/0282823 A1 * | 12/2005 | Breining et al. ............ | 514/256 |
| 2006/0018844 A1 | 1/2006 | Katz et al. | |
| 2006/0057165 A1 * | 3/2006 | Dimitrakoudis et al. ... | 424/239.1 |
| 2006/0078511 A1 | 4/2006 | Friedman | |
| 2007/0009555 A1 | 1/2007 | Borodic | |
| 2007/0135871 A1 * | 6/2007 | Lipov .......................... | 607/89 |
| 2007/0178121 A1 * | 8/2007 | First et al. ................... | 424/239.1 |
| 2007/0218083 A1 * | 9/2007 | Brooks ........................ | 424/239.1 |
| 2007/0218085 A1 * | 9/2007 | Donovan ..................... | 424/239.1 |
| 2008/0021360 A1 * | 1/2008 | Fihe et al. ................... | 602/60 |
| 2008/0092910 A1 * | 4/2008 | Brooks ........................ | 128/898 |
| 2008/0102102 A1 | 5/2008 | Merello et al. | |
| 2008/0118592 A1 | 5/2008 | Ackerman | |
| 2008/0177248 A1 | 7/2008 | Schmidt | |
| 2008/0241183 A1 * | 10/2008 | Palma et al. ................ | 424/193.1 |
| 2009/0010884 A1 * | 1/2009 | Chang et al. ................ | 424/85.5 |
| 2009/0082342 A1 * | 3/2009 | Uldam et al. ............... | 514/221 |
| 2009/0148476 A1 | 6/2009 | Borodic | |
| 2009/0149799 A1 * | 6/2009 | Dacey et al. ................ | 604/20 |
| 2009/0232850 A1 * | 9/2009 | Manack et al. ............ | 424/239.1 |
| 2010/0068232 A1 * | 3/2010 | Key ............................. | 424/239.1 |
| 2010/0266638 A1 * | 10/2010 | Turkel et al. ............... | 424/239.1 |
| 2010/0297182 A1 * | 11/2010 | Tozzi .......................... | 424/239.1 |
| 2011/0130783 A1 * | 6/2011 | Levy et al. .................. | 606/191 |
| 2011/0305735 A1 * | 12/2011 | Cebrian Puche et al. ..... | 424/401 |
| 2011/0318381 A1 * | 12/2011 | Palma et al. ................ | 424/193.1 |
| 2012/0100171 A1 * | 4/2012 | Henry .......................... | 424/190.1 |
| 2013/0230500 A1 * | 9/2013 | Mehdi ......................... | 424/94.1 |

FOREIGN PATENT DOCUMENTS

| | | | |
|---|---|---|---|
| EP | 1289544 A2 | 3/2003 | |
| EP | 1491205 A1 | 12/2004 | |

(Continued)

OTHER PUBLICATIONS

Rebolleda, G et al, European Journal of Ophthalmology, vol. 6(2)., pp. 212-219, Botulinum toxin treatment of Hertwig-Magendie sign, 1996.*

(Continued)

*Primary Examiner* — Albert Navarro
*Assistant Examiner* — Ginny Portner
(74) *Attorney, Agent, or Firm* — Frommer Lawrence & Haug LLP

(57) ABSTRACT

The present invention provides methods for treating a substance addiction-related behavior in a patient with a substance addiction, comprising the step of locally administering a therapeutically effective amount of a botulinum neurotoxin to a location on the patient's body or in the vicinity of the area which comes into contact with a smoking tool or addictive substance, thereby altering, reducing or eliminating sensations associated with behaviors associated with substance addiction. Botulinum neurotoxin may be administered to a dermal, subdermal, mucosal or submucosal location or to a muscle area or in the vicinity of the location to which a smoking tool or addictive substance contacts.

19 Claims, No Drawings

(56) References Cited

FOREIGN PATENT DOCUMENTS

| EP | 1503790 A1 | | 2/2005 | |
|----|------------|---|--------|---|
| EP | 1617862 A2 | | 1/2006 | |
| EP | 1677823 A1 | | 7/2006 | |
| EP | 1767221 | * | 3/2007 | ............ A61K 47/48 |
| EP | 1949909 A1 | | 7/2008 | |
| EP | 1992357 A1 | | 11/2008 | |
| WO | WO-03094955 | | 11/2003 | |
| WO | WO-2004096269 A2 | | 11/2004 | |
| WO | WO-2005084705 A1 | | 9/2005 | |
| WO | WO-2006078998 A2 | | 7/2006 | |
| WO | WO-2006138127 A2 | | 12/2006 | |

OTHER PUBLICATIONS

Morita, Akimichi, Journal of Dermatological Science, 2007, vol. 48, pp. 169-175, Tobacco smoke causes premature skin aging.*
Rachael Lloyd, Jul. 20, 2008, pp. 1-6, Botox Bingers: How much is too much? The Hollywood backlash against the face freezers, dailymail.co.uk/femail/article-/1036837.*
Singh, G. Carter et al, Aesth. Plast Surg., vol. 30, pp. 71-76, 2006, Psychosocial Aspects of Botox in Aesthetic Surgery.*
Dr. Lam, Mar. 24, 2008, SEO Services, pp. 1-2, Managing Fine Lines Around the Mouth.*
Addiction, 1999, vol. 94(6), pp. 923-924, Letter to the Editor, Persistent focal hyperhidrosis following opiate abuse.*
Schnider, P et al, British Journal of Dermatology, vol. 140, pp. 677-680, 1999, A randomized, double blink, placebo-controlled trial of botulinum toxin A for severe axillary hyperhidrosis.*
von Deneen, Karen M et al, Maturitas, vol. 68, pp. 342-345, 2011, Obesity as an addiction: Why do the obese eat more?*
Semchyshyn, N et al, Dermatologic Surgery, vol. 29(5), pp. 490-495, May 2003, Botulinum toxin A Treatment of Perioral Rhytides.*
Schnider, P et al, British Journal of Dermatology, 1997, vol. 136, pp. 548-552, Double blind trial of botulinum A toxin for the treatment of focal hyperhidrosis of the palms.*
Pierce, R. Christopher et al, The Journal of Neuroscience, May 1, 1997, vol. 17(9), pp. 3254-5261, Repeated Cocaine Modifies the Mechanism by which Amphetamine Releases Dopamine.*
Furman, Cheryse A et al, The Journal of Neuroscience, Mar. 11, 2009, vol. 29(10), pp. 3328-3336, Doipamine and Amphetamine Rapidly Increase Dopamine Transporter Trafficking to the Surface: Live-cell Imaging Using Total Internal Reflection Fluorescence Microscopy.*
Out of Control? Botox Addicts, Sep. 17, 1996, The Independent, pp. 1-2.*
Tang-Liu, et al., "Intramuscular Injection of 125I-botulinum Neurotoxin-Complex Versus 125I-botulinum-free Neurotoxin: Time Course of Tissue Distribution," Toxicon 42:461-469 (2003).
Di Chiara G and Imperato A, Drugs abused by humans preferentially increase synaptic dopamine concentrations in the mesolimbic system of freely 5 moving rats. Proc Natl Acad Sci USA 1988;85:5274-5278.
Fiore MC, et al. Treating Tobacco Use and Dependence: 2008 Update-Clinical Practice Guidelines, 2008 [accessed Feb. 6, 2009].
U.S. Food and Drug Administration, The FRD Approves New Drug for Smoking Cessation. FDA Consumer, Jul.-Aug. 2006 [accessed Feb. 6, 2009].
Shantz, et al. Properties and use of Botulinum Toxin and Other Microbial Neurotoxins in Medicine, Microbiol Rev. 56: 80-99 (1992).
Aoki, K., Physiology and pharmacology of therapeutic botulinum neurotoxins, in Kreyden, O., editor, Hyperhydrosis and Botulinum Toxin in Dermatology, Basel, Karger; 2002; 30: pp. 107-116, at 109-110.
Cui, et al., Mechanisms of the antinociceptive effect of subcutaneous BOTOX®: inhibition of peripheral and central nociceptive processing, Naunyn Schmeidebergs Arch Pharmacol 2002; 365 (supp 2): R17.
Aoki, et al., Botulinum toxin type A and other botulinum toxin serotypes: a comparative review of biochemical and pharmacological actions, Eur J. Neurol2001: (suppl5); 21-29).
Hashim, Hashim, Dr. and Abrams, Paul; Treatment options for the overactive bladder syndrome; Therapy, (Nov. 2005) vol. 2, No. 6, pp. 921-936.
Dabrowski, E. et al., Botulinum Toxin as a Novel Treatment for Self Mutilation in Lesch-Nyhan Syndrome; Ann Neurol; 52(3): S157; Abstract.
Diagnostic and Statistical Manual of Mental Disorders 4th Ed.; Published by the American Psychiatric Association Washington, D.C.; pp. 108-116.
Schnider P, et al., Double-blind trial of botulinum A toxin for the treatment of focal of the palms Br J Dermatol 1997; 136: 548-52.
Schnider P, et al. Uses of botulinum toxin. (Letter) Lancet 1997; 349:953.

* cited by examiner

USE OF BOTULINUM NEUROTOXIN TO TREAT SUBSTANCE ADDICTIONS

CROSS-REFERENCE TO RELATED APPLICATION

This application claims the benefit of priority of U.S. Provisional Application Ser. No. 61/247,278, filed Sep. 30, 2009. The foregoing application is incorporated herein by reference in its entirety.

FIELD OF THE INVENTION

This application relates to the use of neurotoxin for treating substance addiction-related behaviors. In particular, botulinum neurotoxin is applied locally to the mouth, nose or fingers of a patient addicted to, for example, smoking or another form of substance addiction to alter familiar sensations, and in turn alter behaviors which facilitate the habit-forming acts.

BACKGROUND OF THE INVENTION

The present invention relates to a method for ceasing smoking and substance addiction-related behaviors. In particular, the present invention includes a method for altering familiar sensations and ritualistic behaviors associated with smoking and substance addiction by peripheral administration of a Clostridial toxin to bodily locations on or in the mouth, nose and fingers, or in the vicinity of such locations which come into contact with a smoking tool or addictive substance.

Smoking is a practice where a substance, most commonly tobacco, is burned and the smoke tasted or inhaled. This is the primary practiced route of administration for recreational drug use, as combustion releases the active substances in drugs, such as nicotine or tetrahydrocannabinol (THC), and makes them available for absorption through the lungs. An estimated 43.4 million people or 19.8% of all adults (aged 18 years and older) in the United States currently smoke cigarettes (Centers for Disease Control and Prevention website, 2009). Most tobacco smokers begin during adolescence or early adulthood. Smoking contributes to numerous medical problems and an early death in approximately one-third of smokers. Although personality and social factors may make people likely to smoke, the actual habit is a function of operant conditioning (Covino and Bottari. Hypnosis, Behavioral Theory, and Smoking Cessation. *Journal of Dental Education* 2001; 65:340-347).

During the early stages, smoking provides pleasurable sensations because of its action on the dopamine system and thus serves as a source of positive reinforcement (Di Chiara G, Imperato A. Drugs abused by humans preferentially increase synaptic dopamine concentrations in the mesolimbic system of freely moving rats. *Proc Natl Acad Sci USA*. 1988; 85:5274-5278). After an individual has smoked for many years, the avoidance of withdrawal symptoms (e.g., irritability, anxiety, difficulty concentrating, increased appetite) and negative reinforcement become the key motivations. There is also a substantial psychological aspect to smoking. People who smoke tend to rationalize their behavior, believing that smoking provides comfort, relieving stress for example.

In general, substance addiction is a pathological condition involving a compulsion to continue using the substance, whether it be chewing tobacco or recreational drugs such as marijuana or cocaine, despite the negative consequences. Like tobacco smoking, other substance addictions involve not only a physical component, most often a chemical dependency, but also a substantial psychological component accompanied by ritualistic behavior, such as those involved in the act of smoking or sniffing the addictive substance.

Among current U.S. adult smokers, 40% have stopped smoking for at least one day within a twelve month time period because they were trying to quit smoking. Because smoking (e.g., tobacco or other recreational drugs) is very addictive, both physically and psychologically, most smoking cessation methods have poor success rates, and quitting often requires repeated intervention (Centers for Disease Control and Prevention website, 2009). Various methods and products are used in attempts to quit smoking, including nicotine gum, inhaler, nasal spray, lozenge, patch, counseling, and prescription normicotine medications, such as bubropion SR (Zyban®) and varenicline tartrate (Chantix®) (Fiore M C, et al. Treating Tobacoo Use and Dependence: 2008 Update—Clinical Practice Guidelines, 2008 [accessed 2009 Feb. 6]; U.S. Food and Drug Administration. The FRD Approves New Drug for Smoking Cessation. FDA Consumer, July-August 2006 [accessed 2009 Feb. 6]).

Many current treatments may also fail because they do not address all aspects of the substance addiction, particularly the psychological aspect. Not only do substance addicts form a chemical dependency on the active drug, but they also form a psychological dependency based on familiarity and repetitive motor activity, including for example the familiarity of holding a cigarette (tobacco or marijuana) in one's hands, flicking the cigarette, drawing it to one's mouth, and holding the cigarette between one's lips. It may be this habitual/ritualistic behavior and sense of familiarity that the majority of current treatments fail to address.

At present, botulinum neurotoxins are being used in clinical settings for the treatment of neuromuscular disorders characterized by hyperactive skeletal muscles. Botulinum neurotoxin serotype A was approved in 1989 by the U.S. Food and Drug Administration for the treatment of essential blepharospasm, strabismus and hemifacial spasm in patients over the age of twelve. In 2000, the FDA approved for the treatment of cervical dystonia commercial preparations of serotype A and serotype B botulinum neurotoxin, and in 2002 the FDA approved for the cosmetic treatment of certain hyperkinetic (glabellar) facial wrinkles a serotype A botulinum neurotoxin. In 2004, botulinum neurotoxin was approved by the FDA for the treatment of hyperhidrosis. Non-FDA approved uses include hemifacial spasm, spasmodic torticollis, oromandibular dystonia, spasmodic dysphonia and other dystonias, tremor, myofascial pain, temporomandibular joint dysfunction, migraine, and spasticity.

The success of botulinum neurotxin serotype A to treat a variety of clinical conditions has led to interest in other botulinum neurotoxin serotypes. A botulinum neurotoxin serotype B (BT-B) preparation (MyoBloc®) is available from Solstice Neurosciences of Malvern, Pa. Similar therapeutic effects are seen after about 150-200 mouse units of Botox® or about 500-750 mouse units of Dysport®. This indicates a conversion factor for Botox® to BT-B in the order of 40-70 and for Dysport® to BT-B of 10-20. (See Dressler, Botulium Toxin Type B: Where Do We Stand?, 114 Eur Neurol, 46:113-114 (2001)).

The anaerobic, gram positive bacterium *Clostridium botulinum* produces a potent polypeptide neurotoxin, botulinum neurotoxin. To date, seven immunologically distinct botulinum neurotoxins have been characterized: serotypes A, B, $C_1$, D, E, F, and G. Of these, botulinum neurotoxin serotype A is recognized as one of the most lethal naturally occurring agents.

It is postulated that the botulinum neurotoxins bind with high affinity to cholinergic motor neurons, are transferred into the neuron and effectuate blockade of the presynaptic release of acetylcholine. All of the botulinum neurotoxin serotypes are purported to inhibit release of acetylcholine at the neuromuscular junction, and they do so by affecting different neurosecretory proteins and/or cleaving these proteins at different sites. It is believed that differences in the site of inhibition are responsible for the relative potency and/or duration of action of the various botulinum toxin serotypes.

Despite the apparent difference in serotype binding, it is thought that the mechanism of botulinum activity for each serotype is similar and involves at least three steps. First, the toxin binds to the presynaptic membrane of a target cell. Second, the toxin enters the plasma membrane of the effected cell wherein an endosome is formed. The toxin is then translocated through the endosomal membrane into the cytosol. Third, the botulinum neurotoxin appears to reduce a synaptosomal-associated protein (SNAP) disulfide bond resulting in disruption in zinc ($Zn^{++}$) endopeptidase activity, which selectively cleaves proteins essential for recognition and docking of neurotransmitter-containing vesicles with the cytoplasmic surface of the plasma membrane, and fusion of the vesicles with the plasma membrane.

The molecular weight of the botulinum neurotoxin protein molecule, for all seven of the known botulinum neurotoxin serotypes, is about 150 kD. Interestingly, the botulinum neurotoxins are released by Clostridial bacterium as complexes comprising the 150 kD botulinum neurotoxin protein molecule along with associated non-toxic proteins. Thus, the botulinum neurotoxin serotype A complex can be produced by Clostridial bacterium as 900 kD, 500 kD and 300 kD forms. Botulinum neurotoxin serotypes B and $C_1$ are produced as only a 500 kD complex. Botulinum neurotoxin serotype D is produced as both 300 kD and 500 kD complexes. Finally, botulinum neurotoxin serotypes E and F are produced as only approximately 300 kD complexes. The complexes (i.e., molecular weight greater than about 150 kD) are believed to contain anon-toxic hemagglutinin protein and a non-toxic non-hemagglutinin protein. These two non-toxic proteins (which along with the botulinum neurotoxin molecule can comprise the relevant neurotoxin complex) may act to provide stability against denaturation to the botulinum neurotoxin molecule and protection against digestive acids when toxin is ingested.

All the botulinum neurotoxin serotypes are made by *Clostridium botulinum* bacteria as inactive single chain proteins which must be cleaved or nicked by proteases to become neuroactive. The bacterial strains that make botulinum neurotoxin serotypes A and G possess endogenous proteases and serotypes A and G can therefore be recovered from bacterial cultures in predominantly their active form. By contrast, botulinum neurotoxin serotypes $C_1$, D, and E are synthesized by nonproteolytic strains and are therefore typically inactivated when recovered from culture. Serotypes B and F are produced by both proteolytic and nonproteolytic strains and therefore can be recovered in either the active or inactive form. However, even the proteolytic strains that produce, for example, the botulinum neurotoxin type B serotype only cleave a portion of the toxin produced. The exact proportion of nicked to unnicked molecules depends on the length of incubation and the temperature of the culture. Therefore, a certain percentage of any preparation of, for example, the botulinum neurotoxin serotype B is likely to be inactive, possibly accounting for a lower potency of botulinum neurotoxin serotype B as compared to botulinum neurotoxin serotype A. The presence of inactive botulinum neurotoxin molecules in a clinical preparation will contribute to the overall protein load of the preparation, which has been linked to increased antigenicity, without contributing to its clinical efficacy.

In vitro studies have indicated that botulinum neurotoxin inhibits potassium cation-induced release of both acetylcholine and norepinephrine from primary cell cultures of brainstem tissue. Additionally, it has been reported that botulinum neurotoxin inhibits the evoked release of both glycine and glutamate in primary cultures of spinal cord neurons and that in brain synaptosome preparations, botulinum neurotoxin inhibits the release of each of the neurotransmitters acetylcholine, dopamine, norepinephrine, CGRP and glutamate.

High quality crystalline botulinum neurotoxin serotype A can be produced from the Hall A strain of *Clostridium botulinum* with characteristics of $3\times10^7$ U/mg, an $A_{260}/A_{278}$ of less than 0.60 and a distinct pattern of banding on gel electrophoresis. The known Shantz process can be used to obtain crystalline botulinum neurotoxin serotype A, as set forth in Shantz, et al. (See Shantz, et al. Properties and use of Botulinum Toxin and Other Microbial Neurotoxins in Medicine, Microbiol Rev. 56: 80-99 (1992)). Generally, the botulinum neurotoxin serotype A complex may be isolated and purified from an anaerobic fermentation by cultivating botulinum neurotoxin serotype A in a suitable medium. Raw toxin may be harvested by precipitation with sulfuric acid and concentrated by ultramicrofiltration. Purification may be carried out by dissolving the acid precipitate in calcium chloride. The toxin may then be precipitated with cold ethanol, dissolved in sodium phosphate buffer and centrifuged. Upon drying there may then be an approximately 900 kD crystalline botulinum neurotoxin serotype A complex with a specific potency of $3\times10^7$ $LD_{50}$ U/mg or greater (LD, lethal dose). This known process can also be used, upon separation out of the non-toxic proteins, to obtain pure botulinum neurotoxins, such as for example: (1) purified botulinum toxin type A with an approximately 150 kD molecular weight with a specific potency of $1-2\times10^8$ $LD_{50}$ U/mg or greater; (2) purified botulinum neurotoxin serotype B with an approximately 156 kD molecular weight with a specific potency of $1-2\times10^8$ $LD_{50}$ U/mg or greater; and (3) purified botulinum neurotoxin serotype F with an approximately 155 kD molecular weight with a specific potency of $1-2\times10^7$ $LD_{50}$ U/mg or greater.

Already prepared and purified botulinum neurotoxins and toxin complexes suitable for preparing pharmaceutical formulations can be obtained from List Biological Laboratories, Inc., Campbell, Calif.; the Centre for Applied Microbiology and Research, Porton Down, U.K.; Wako (Osaka, Japan), as well as from Sigma Chemicals of St. Louis, Mo.

Two commercially available botulinum type A preparations for use in humans are BOTOX® available from Allergan, Inc., of Irvine, Calif., and Dysport® available from Beaufour Ipsen, Porton Down, England. BOTOX® consists of a purified botulinum neurotxin serotype A complex, albumin and sodium chloride packaged in sterile, vacuum-dried form.

Clinical effects of peripheral administration of botulinum neurotoxin serotype A are typically observed within 24-48 hours of administration and sometimes within a few hours. When used to induce muscle paralysis, symptomatic relief from, for example, a single intramuscular injection of botulinum toxin type A may last approximately three months; however, under certain circumstances effects have been known to last for several years.

Citation or identification of any document in this application is not an admission that such document is available as prior art to the present invention.

SUMMARY OF THE INVENTION

The present invention provides methods for treating substance addiction in a patient addicted to, for example, smoking or sniffing harmful substances, comprising the step of administering a therapeutically effective amount of a botulinum neurotoxin to a location on the patient's body, or to the vicinity of the location, which comes into contact with a smoking tool or addictive substance, thereby altering, reducing or eliminating sensations associated with the initiation of substance addiction-related behaviors.

The botulinum neurotoxin is either a complex or a pure molecule [e.g. about 150 kD molecule], such as a botulinum neurotoxin serotypes A, B, $C_1$, D, E, F or G. Preferably, the botulinum neurotoxin is serotype A or serotype B. Most preferably, the botulinum neurotoxin is serotype A. The effects of the botulinum neurotoxin may persist for about 1 month to about 5 years. The botulinum neurotoxin can be a recombinantly made botulinum neurotoxin, such as botulinum neurotoxin produced by *E. coli*. In addition or alternatively, the botulinum neurotoxin can be a modified neurotoxin, that is, a botulinum neurotoxin which has at least one of its amino acids deleted, modified or replaced, as compared to a native, or the modified botulinum neurotoxin can be a recombinant produced botulinum neurotoxin or a derivative or fragment thereof.

A method according to the present invention may be carried out by local peripheral administration of a therapeutically effective amount of botulinum neurotoxin to a patient with a substance addiction, for example, an addiction to smoking tobacco or marijuana or sniffing cocaine.

Local administration of the botulinum neurotoxin may be by a transdermal or transmucosal route (e.g., by application of a patch, cream, ointment, or lotion vehicle comprising botulinum neurotoxin), subdermal route (e.g., subcutaneous), an intradermal route, or intramuscular route.

A hypothesized physiological reason for the efficacy of the present invention is to reduce, inhibit or eliminate particular sensory input (afferent) from the periphery into the central nervous system (CNS) (including to the brain), which sensory input is believed to precede substance addiction-related behaviors. Such sensory input can be attenuated or eliminated by targeting with botulinum neurotoxin sensory neurons located in or under the skin (dermal or subdermal) or mucosa (mucosal or submucosal) or located within muscle tissues (intramuscular).

The therapeautically effective amount of a botulinum neurotoxin used according to the present invention is typically much less than the amount of toxin that would be used to paralyze a muscle (and is even typically less than the amount of the toxin used to reduce a rigid muscle tone by a clinically significant amount). This is because it is desirable not to paralyze a muscle or to reduce the tone of a rigid muscle when carrying out the methods described herein, but to reduce sensory output from sensory neurons located in or under the skin or in a muscle. Additionally, the amount of botulinum neurotoxin is selected with a volume to preferably achieve a toxin distribution to multiple sites of undesirable afferent sensory signals, such as from spindle fibers or secretory cells in the skin, mucosa, subdermis, or submucosa.

Thus, the instant invention is a pharmacologic method for treating substance addiction-related behaviors, characterized by repetitive motor activity. The invention may be practiced by administering a therapeutically effective amount of a botulinum neurotoxin to dermal, intradermal, subdermal, mucosal or submucosal sensory neurons which apparently generate an urge or sensation which precedes behaviors associated with substance addiction, particularly those sensory neurons that contact a smoking tool or addictive substance. Alternatively, the toxin may be administered locally to the muscle or muscle group which appears to initiate or facilitate the repetitive motor activity (e.g., cigarette flicking, raising a smoking tool to one's mouth, sucking on or chewing tobacco, sniffing cocaine). Thus, neurotoxin administration may be to the mouth, nose or hands/fingers of an addict. Administration of botulinum neurotoxin may reduce, inhibit or eliminate behaviors associated with substance addiction within a few hours or within a few days after administration.

It is noted that in this disclosure and particularly in the claims and/or paragraphs, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

DETAILED DESCRIPTION

The present invention provides a method of treating substance addiction-related behaviors in a patient, comprising the step of locally administering a therapeutically effective dose of a botulinum neurotoxin to a location on the patient's body which comes into contact with a smoking tool or addictive substance, thereby altering sensations typically experienced by substance addicts.

"Substance addiction" refers to an uncontrollable compulsion to consume a substance (e.g., tobacco, marijuana, cocaine) to the point where stopping the consumption would cause emotional, mental, or physical reactions.

"Substance addiction-related behaviors", "habitual behaviors", or "ritualistic behaviors" may be used interchangeably herein and include but are not limited to lighting a smoking tool, flicking ashes from a smoking tool, drawing a smoking tool to one's mouth, pursing one's lips and inhaling smoke from a smoking tool, and holding a smoking tool in one's hands or between one's lips, and sniffing, chewing, or sucking on an addictive substance.

As used herein "smoking" refers to a practice where a substance is burned and the smoke tasted or inhaled. A "smoker" is a patient who practices the act of smoking.

A "smoking tool" may refer to a cigarette (mass-produced or hand-rolled), cigar, pipe, hookah (water pipe), bong, or any tool from which a substance such as but not limited to tobacco, marijuana and/or cocaine may be smoked or sniffed.

An "addictive substance" may refer to any substance which a patient feels compelled to consume, including but not limited to tobacco (e.g., cigarettes or chewing tobacco), *Cannabis* (marijuana), cocaine, heroine, LSD (acid), MDMA (ecstasy), and any recreational drug including but not limited to synthetic drugs.

"Treat", "treating" or "treatment" may mean a reduction in the occurrence of or absence of the behavior. Thus, treating includes some reduction (including but not limited to behavior practiced for fewer than, or appears in fewer than, six hours out of a twenty-four hour period), significant reduction (including but not limited to behavior practiced for fewer than, or appears in fewer than, three hours out of a twenty-four hour period), near total absence (including but not limited to behavior practiced for fewer than, or appears in fewer than, one hour out of a twenty-four hour period), and total absence of the behavior. An effect of treatment may not appear clinically for between 1 to 7 days after administration of a botulinum neurotoxin to a patient.

"About" means approximately or nearly and in the context of a numerical value or range set forth herein means 10% of the numerical value or range recited or claimed.

"Botulinum neurotoxin" may mean a botulinum neurotoxin as either pure toxin or complex.

In one embodiment, the botulinum neurotoxin may be botulinum neurotoxin serotype A, B, $C_1$, D, E, F and G. In another embodiment, the botulinum neurotoxin is serotype A or serotype B. In yet another embodiment, the botulinum neurotoxin is serotype A.

As used herein, a "therapeutically effective" amount or dose of botulinum toxin refers to an amount of the botulinum neurotoxin which is sufficient to inhibit a sensory output from a muscle, mucosa, submucosa, dermis or subdermis to the CNS, but which is insufficient to cause either clinically significant muscle paralysis, weakness or hypotonicity (e.g., rendering the muscle non-functional or non-usable or not able to bear weight). Typically, a therapeutically effective dose of botulinum toxin induces a change in substance addiction-related behaviors or a sensation associated with the behavior. For example, a change in sensation may include but is not limited to a slight moderate numbness of the body location, or a change in sensitivity or awareness of touch in that location. It is to be understood that the therapeutically effective amount or dose refers to the amount of botulinum neurotoxin that acts locally on the sensory neuron or muscle of interest. While botulinum neurotoxin in excess may be topically applied, for example, to a location on the dermis, the therapeutically effective amount refers only to that neurotoxin which penetrates one or more layers of the dermis and acts locally on the neurons or muscles to cause a change in sensation or behavior. It is to be understood that when applied topically in excess, for example, in the form of a cream or ointment, a portion of the toxin may be unintentionally rubbed or washed from the dermis and will not reach the target area. Thus, a therapeutically effective amount or dose refers to the neurotoxin which remains at the local target site and acts on the sensory neuron(s) or muscle(s).

The therapeutically effective amount of the botulinum neurotoxin administered according to a method within the scope of the disclosed invention may vary according to age, weight, height, sex, muscle mass, area of target region, number of applications sites, skin thickness, responsiveness to therapy and other patient variables known to the attending physician. For example, the extent of the area of tissue influenced is believed to be proportional to the volume of neurotoxin injected, while the quantity of the suppressant effect is, for most dose ranges, believed to be proportional to the concentration of a botulinum neurotoxin administered. The amount may also depend on the solubility characteristics of the botulinum neurotoxin chosen. Methods for determining the appropriate route of administration and dosage are generally determined on a case by case basis by the attending physician. Such determinations are routine to one of ordinary skill in the art (See for example, Harrison's Principles of Internal Medicine (1998), edited by Anthony Fauci et al., 14$^{th}$ edition, published by McGraw Hill).

Typically, about 0.1 unit to about 50 units of a botulinum neurotoxin serotype A (such as BOTOX®) is administered per site (e.g., by injection or topical application), per patient treatment session. For a botulinum neurotoxin serotype A such as DYSPORT®, about 0.2 units to about 125 units of the botulinum neurotoxin serotype A are administered per injection site, per patient treatment session. For a botulinum neurotoxin serotype B such as MYOBLOC®, about 10 units to about 1500 units of the botulinum neurotoxin serotype B are administered per injection site, per patient treatment session. In certain embodiments, application of a topical form of botulinum neurotoxin may exceed greater than 50, 125, or 1500 units for BOTOX®, DYSPORT® or MYOBLOCK®, respectively. The dose should be sufficient to inhibit a sensory output from a muscle to the CNS, but insufficient to cause either clinically significant muscle paralysis, weakness or hypotonicity.

In one embodiment, for BOTOX®, about 0.1 unit to about 20 units may be administered; for DYSPORT®, about 0.2 unit to about 100 units may be administered; and, for MYOBLOC®, about 40 units to about 1000 units may be administered per injection site, per treatment session.

In another embodiment, for BOTOX®, about 0.5 unit to about 15 units may be administered; for DYSPORT®, about 1 unit to about 75 units may be administered; and for MYOBLOC®, about 100 units to about 750 units may be administered per injection site, per patient treatment session.

In one embodiment, the neurotoxin may be delivered in multiple doses for each patient treatment session. In another embodiment the neurotoxin is delivered in about 1 to about 10 doses, depending on patient variables. In yet another embodiment the total therapeutically effective dose administered (e.g., about 0.1 unit to about 50 units) is divided evenly amongst multiple injection sites.

In one embodiment, the toxin may be delivered at a concentration including but not limited to 0.4 U/0.1 ml. The concentration will depend on the type of botulinum neurotoxin used and on the target location to which the toxin is applied.

As used herein "local administration" or "local application" means peripheral administration (e.g., by a dermal, subdermal, intradermal, transdermal, subcutaneous, mucosal, submucosal or intramuscular route) of a botulinum neurotoxin, or to the vicinity of, a location on a patient's body by a non-systemic route. Thus, local administration excludes systemic (e.g., to the blood circulation system) routes of administration, such as intravenous administration. "Peripheral administration" refers to administration to the periphery (e.g., to a location on or within a limb, trunk or head of a patient) as opposed to a visceral or gut (e.g., to the viscera). Local administration or application also includes but is not limited to topical application to or injection into a dermal, subdermal, intradermal, transdermal, subcutaneous, mucosal, submucosal or intramuscular body location on a patient. In or to "the vicinity of" a body location refers to a location within about 5 cm$^2$ of the location which comes into contact with a smoking device or addictive substance.

In one embodiment, the body location is inside of or around the opening of the mouth or nose of the patient or to a location on the hand, hands, finger or fingers of the patient.

The body location inside of the patient's mouth may include but is not limited to the mucosal lining or salivary glands, including the parotid or submandibular glands, the sublingual glands and minor salivary glands lining the mucosa of the oral cavity. The body location around the opening of the patient's mouth may include but is not limited to the lips or area immediately surrounding the lips. In another embodiment, the body location is within an about 1 cm$^2$ area surrounding the patient's lips. In yet another embodiment, botulinum toxin is administered locally to the specific region of the lip that contacts the smoking tool or addictive substance (e.g., center of the lip, corners of the mouth, inside area of the lower lip).

In one embodiment, the therapeutically effective dose of botulinum neurotoxin delivered to the inside of the mouth is sufficient to reduce mucosal/salivary secretions of the mouth, thereby having a drying effect on the mouth and lips. Botulinum neurotoxin may be injected directly into the parotid or submandibular glands, the sublingual glands and minor salivary glands lining the mucosa of the oral cavity, including the lips to reduce saliva production by about 50-60%, a single application lasting for up to about 6 months. Such a drying effect may deter a patient from smoking or chewing tobacco, for example, in order to prevent further uncomfortable drying of the oral cavity.

In another embodiment, the body location is on a patient's nose. In yet another embodiment, botulinum toxin may be applied locally to the skin surrounding the nostrils, to the skin within the nostrils or on the mucosa lining the nasal septum or nasal lining.

In one embodiment, the body location is on a patient's hand or hands. The hand area may be but is not limited to a thumb, index finger, middle finger, and a combination thereof. In another embodiment, botulinum toxin may be administered locally to the specific region of the thumb, index finger, and/or middle finger which comes into contact with the smoking tool (e.g., the medial regions of the index finger and middle finger or the distal regions of the thumb and index finger).

In yet another embodiment, the local administration of the botulinum neurotoxin is to a dermal, subdermal, intradermal, transdermal, subcutaneous, mucosal, submucosal or intramuscular location or to a muscle or in the vicinity of a location with which a smoking tool or addictive substance contacts. Local administration to the dermal location may be via but is not limited to transdermal or transmucosal delivery. The transdermal or transmucosal delivery may be via but is not limited to a patch, cream, ointment or lotion vehicle comprising botulinum neurotoxin. In still another embodiment, local administration to the muscle is by intramuscular injection.

Thus, an application of the botulinum toxin is selected to focus on the sensory neurons or muscles which initiate the observed substance addiction-related behavior(s).

Without wishing to be bound by theory, a physiological mechanism may be proposed for the efficacy of the present invention. Muscles have a complex system of innervation and sensory output. Thus, anterior motor neurons located in each segment of the anterior horns of the spinal cord gray matter give rise to efferent alpha motor neurons and efferent gamma motor neurons that leave the spinal cord by way of the anterior roots to innervate skeletal (extrafusal) muscle fibers. The alpha motor neurons cause contraction of extrafusal skeletal muscle fibers while the gamma motor neurons innervate the intrafusal fibers of skeletal muscle. Other, afferent sensory neurons project from muscle spindle and golgi tendon organs and act to transmit information relating to various muscle parameter status to the spinal cord, cerebellum and cerebral cortex.

These afferent motor neurons which relay sensory information from the muscle spindle include type Ia and type II sensory afferent neurons (See e.g. pages 686-688 of Guyton A. C. et al., Textbook of Medical Physiology, W. B. Saunders Company 1996, ninth edition). Botulinum neurotoxin can function to reduce transmission of sensory information from muscle type Ia afferent neurons (See Aoki, K., Physiology and pharmacology of therapeutic botulinum neurotoxins, in Kreyden, O., editor, Hyperhydrosis and Botulinum Toxin in Dermatology, Basel, Karger; 2002; 30: pages 107-116, at 109-110). It has been hypothesized that botulinum neurotoxin can act directly on muscle cell sensory afferents to modify signals from these afferents to the CNS (See e.g. Brin, et al., Botulinum toxin type A: pharmacology, in Mayer N., editor, Spasticity: etiology, evaluation, management and the role of botulinum toxin, 2002; pages 110-124, at 112-113; Cui, et al., Mechanisms of the antinociceptive effect of subcutaneous BOTOX®: inhibition of peripheral and central nociceptive processing, Naunyn Schmiedebergs Arch Pharmacol 2002; 365 (supp 2): R17; Aoki, et al., Botulinum toxin type A and other botulinum toxin serotypes: a comparative review of biochemical and pharmacological actions, Eur J. Neurol 2001: (suppl 5); 21-29). Thus, botulinum neurotoxin can cause an altered sensory output from muscle to CNS and brain.

In theory, substance addiction-related behaviors may be attributed to disinhibition of a CNS control process. Thus, a disinhibition reverberatory circuit may exist between the head of the caudate nucleus and the thalamus and between the thalamus and the frontorbito neurons, which is sensitive to signals arising from peripheral sensory information afferent from muscle neurons. Administration of a botulinum neurotoxin to a muscle or skin to reduce sensory output from the muscle can permit the brain to regain adequate inhibition control of the substance-addiction-related behaviors by preventing central generation of a premonitory urge to perform the addictive behavior.

It has been hypothesized that signals transmitted by afferent nerves which innervate muscles (e.g., muscle spindle fibers and muscle pain fibers) or from sensory structures in the skin or subdermally induce a sensory state which contributes in susceptible individuals to the generation of compulsive-type behaviors (See WO12004/096269 e.g. self-mutilation, obsessive hand washing, and hair pulling). According to such a hypothesis, afferent signal from muscles or skin structures provide sensory information to the brain which then leads to the generation of a motor output in susceptible individuals. Thus, a local administration of a low dose of a botulinum toxin to muscle spindle fibers, pain fibers or other sensors in or in the vicinity of a muscle can act to alter the neural signal afferent output from these muscles to the brain and thereby decreasing neural (to brain) input and inhibit the undesirable behavior by preventing generation of a premonitory urge.

Peripheral administration permits a botulinum neurotoxin to be locally administered at a site, at or near a patient's dermis, subdermis, mucosa, submucosa or muscle that has a direct effect on the neurons involved in behaviors associated substance addiction. The botulinum neurotoxins used in accordance with the invention disclosed herein may inhibit transmission of chemical or electrical signals between select neuronal groups that are involved in generation of the urge or impulse to perform behaviors associated with substance addiction. The botulinum neurotoxins preferably are not cytotoxic to the cells that are exposed to the toxin. The botulinum neurotoxin may inhibit neurotransmission by reducing or preventing exocytosis of neurotransmitter from the neurons exposed to the toxin. Alternatively, the applied botulinum neurotoxins may reduce neurotransmission by inhibiting the generation of action potentials of the neurons exposed to the toxin.

The suppressive effects provided by the botulinum neurotoxins may persist for a relatively long period of time, for example, for more than two months, and potentially for several years.

Examples of botulinum neurotoxins within the scope of the present invention include botulinum neurotoxin type A, which may be preferred due to its high potency in humans, ready availability, and known use for the treatment of skeletal and smooth muscle disorders when locally administered by intramuscular injection. The present invention also includes the use of (a) botulinum neurotoxins obtained or processed by bacterial culturing, toxin extraction, concentration, preservation, freeze drying, and/or reconstitution; and/or (b) modified or recombinant neurotoxins, that is neurotoxins that have had one or more amino acids or amino acid sequences deliberately deleted, modified or replaced by known chemical/biochemical amino acid modification procedures or by use of known host cell/recombinant vector recombinant technologies, as well as derivatives or fragments of neurotoxins so made. These neurotoxin variants retain the ability to inhibit neurotransmission between or among neurons, and some of these variants may provide increased durations of inhibitory effects as compared to native neurotoxins, or may provide enhanced binding specificity to the neurons exposed to the neurotoxins.

These neurotoxin variants may be selected by screening the variants using conventional assays to identify neurotoxins that have the desired physiological effects of inhibiting neurotransmission.

Botulinum neurotoxins for use according to the present invention may be stored in lyophilized, vacuum dried form in containers under vacuum pressure or as stable liquids. Prior to lyophilization the botulinum toxin may be combined with pharmaceutically acceptable excipients, stabilizers and/or carriers, such as albumin. The lyophilized material may be reconstituted with saline or water to create a solution or composition containing the botulinum toxin to be administered to the patient.

Other preparations of botulinum toxin are as follows:
Type A (Dysport®): Powder for solution for injection. Uncoloured Type I glass vial containing a sterile white lyophilized powder.
Type B toxin (Myobloc®) Botulinum toxin type B (Myobloc®) is commercially available as a clear, colorless to light yellow solution of the drug in sterile water for injection. Each vial of Myobloc® injection contains 5000 units/mL of botulinum toxin type B; each mL of the injection also contains 0.5 mg of albumin human (to minimize adsorption of the toxin to the glass vial), 2.7 mg of sodium succinate, and 5.8 mg of sodium chloride. The commercially available injection of botulinum toxin type B (Myobloc®) has a pH of approximately 5.6.

Although the composition may only contain a single type of neurotoxin, such as botulinum neurotoxin serotype A, as the active ingredient to suppress neurotransmission, other therapeutic compositions may include two or more types of neurotoxins, which may provide enhanced therapeutic effects for treatment of the substance addiction-related behavior. For example, a composition administered to a patient may include botulinum neurotoxin serotype A and botulinum neurotoxin serotype B. Administering a single composition containing two different neurotoxins may permit the effective concentration of each of the neurotoxins to be lower than if a single neurotoxin is administered to the patient while still achieving the desired therapeutic effects.

The botulinum neurotoxin may be administered by any suitable method as determined by the attending physician. The methods of administration permit the botulinum neurotoxin to be administered locally to a selected target tissue. Methods of administration include injection of a solution or composition containing the botulinum neurotoxin and topical application, as described above, and include implantation of a controlled release system that controllably releases the neurotoxin to the target tissue. Such controlled release systems reduce the need for repeat applications.

Implants useful in practicing the methods disclosed herein may be prepared by mixing a desired amount of a stabilized neurotoxin (such as non-reconstituted BOTOX®) into a solution of a suitable polymer dissolved in methylene chloride. The solution may be prepared at room temperature. The solution can then be transferred to a Petri dish and the methylene chloride evaporated in a vacuum desiccator. Depending upon the implant size desired and hence the amount of incorporated neurotoxin, a suitable amount of the dried neurotoxin incorporating implant is compressed at about 8000 p.s.i. for 5 seconds or at 3000 p.s.i. for 17 seconds in a mold to form implant discs encapsulating the neurotoxin (See e.g., Fung L. K. et al., Pharmacokinetics of Interstitial Delivery of Carmustine 4-Hydroperoxycyclophosphamide and Paclitaxel From a Biodegradable Polymer Implant in the Monkey Brain, Cancer Research 58; 672-684: 1998).

Local administration of a botulinum neurotoxin can provide a high, local therapeutic level of the toxin. A controlled release polymer capable of long term, local delivery of a botulinum neurotoxin to a target muscle permits effective dosing of a target tissue. A suitable implant, as set forth in U.S. Pat. No. 6,306,423 entitled "Neurotoxin Implant", allows the direct introduction of a chemotherapeutic agent to a target tissue via a controlled release polymer. The implant polymers used are preferably hydrophobic so as to protect the polymer incorporated neurotoxin from water induced decomposition until the toxin is released into the target tissue environment.

The invention will now be further described by way of the following non-limiting examples.

EXAMPLES

The following non-limiting examples provide those of ordinary skill in the art with specific methods to treat conditions within the scope of the present invention and are not intended to limit the scope of the invention. In the following examples various modes of non-systemic administration of a botulinum neurotoxin may be carried out. For example, by intramuscular injection, subcutaneous injection, topical application or by implantation of a controlled release implant.

Example 1

Injection at the Mucocutaneous Junction of the Lower Lip

A 30 year old male who wishes to quit smoking tobacco cigarettes presents to his physician for assistance. A total of 32 units of botulinum toxin type A (DYSPORT®) is injected intradermally into the lower lip at the mucocutaneous border, divided over 6 injection sites placed equally apart (3 injections into upper lip and 3 injections into lower lip, the central injections contain 8 units and the lateral injections contain 4 units). The lip is not massaged after the injections to prevent deeper penetration into the muscular layer. The patient experiences a slight to moderate numbing sensation at and adjacent to the injections sites. The patient finds it more difficult and less pleasing to hold the cigarette between his lips. Within 1 to 7 days, this negative association leads to less of an urge to smoke, thus leading to his long term cessation of smoking. Thus, the application of botulinum toxin at the site of application changes the sensation such that when the patient resumes the habit, the alteration in sensation leads to an alteration in behavior.

Example 2

Injections into the Skin Surrounding the Lips, at the Oral Commissure

A 30 year old male who wishes to quit smoking cigarettes presents to his physician for assistance. He routinely places the cigarette at his left oral commissure. A total of 2 units of botulinum toxin type A (BOTOX®) are injected intradermally around the oral commissure at 2 injection sites. One injection of 1 unit botulinum toxin type A is given intradermally away from the mucocutaneous junction above the left oral commissure and one injection of 1 unit of botulinum toxin type A is placed intradermally away from the mucocutaneous junction below the left oral commissure. The lip is not massaged after the injection to prevent deeper penetration into the muscular layer. The patient experiences a slight to moderate numbing sensation at and adjacent to the injections sites. The patient finds it more difficult and less pleasing to hold the cigarette between his lips. Within 1 to 7 days, this alteration in sensation and negative association leads to less of an urge to smoke, thus leading to his long term cessation of smoking.

Example 3

Injection at the Mucocutaneous Junction of the Lower Lip

A 50 year old female has been a long time smoker and has decided to quit smoking. She presents to her physician for assistance. She is injected along the upper and lower lip mucocutaneous border with a total of 160 units of Myobloc® serotype B botulinum toxin divided into 6 injection sites (3 injections into upper lip and 3 injections into lower lip). The central injections contain 40 units and the lateral injections contain 20 units. The injection sites are not massaged following injection. The patient experiences a slight to moderate numbing sensation at and adjacent to the injections sites. The patient finds it more difficult and less pleasing to hold the cigarette between her lips. Within 1 to 7 days, this alteration in sensation and negative association leads to less of an urge to smoke, thus leading to her long term cessation of smoking.

Example 4

Injection of the Skin of Fingers

A 30 year old female who wishes to quit smoking tobacco cigarettes presents to her physician for assistance. A total of 50 units of type A botulinum toxin is injected in the subdermal region at the sites where the cigarette contacts the skin of her fingers. A 100 unit vial of BOTOX® is reconstituted with 2 cc of saline and a total of 1 cc is injected into the subdermal space of each finger at 3 separate sites. The near total loss of sensation between her middle and index fingers makes it difficult and less pleasing to hold a cigarette. This alteration in sensation and negative association breaks her habit of holding a cigarette. Within 1-7 days the patient has less of an urge to smoke, leading to her long term cessation of smoking.

Example 5

Injection Placed Beneath the Mucosa of the Lip and into the Salivary Glands

A 30 year old male wishes to break his habit of chewing tobacco. He presents to his physician for assistance. A total of 4 units of botulinum toxin type A (BOTOX®) is injected submucosally into the lower lip, divided over 4 injection sites (1 unit per injection site), placed equally apart. The lip is not massaged after the injection to prevent deeper penetration into the muscular layer. The patient's salivary glands are also injected so as to minimize salivary secretions, thus having a slight drying effect on the mouth. The patients experiences a slight to moderate numbness of the lower lip. Persistent, he attempts chewing tobacco but finds it displeasing due to (1) lack of sensation on his lip and (2) an uncomfortable dryness in his mouth. These alterations in sensation and negative associations break him of his tobacco-chewing habit. Within 1-7 days the patient has less of an urge to chew on tobacco, leading to his long term cessation of the addiction.

Example 6

Injection Submucosally

A 30 year old male who wishes to quit smoking marijuana (he has formed an addiction following long-term medical usage) presents to his physician for assistance. A total of 2 units of botulinum toxin type A (BOTOX®) is injected submucosally such that the botulinum toxin is exposed to the minor salivary glands on either sides of the mouth, producing dryness. Persistent, the man tries to enjoy a session of smoking, but for the first time finds it very displeasing due to the exceptional drying sensation in his mouth and near his lips. This alteration in sensation and negative association breaks him of his marijuana smoking addiction. Within 1-7 days the patient has less of an urge to smoke, leading to his long term cessation of smoking.

Example 7

Topical Application

A 50 year old female has been a long time smoker and is concerned about emphysema. She presents to her physician for assistance, but warns her that she has a terrible fear of needles. Rather than inject the woman, the physician applies 50 units of botulinum toxin type A on the skin by soaking gauze at the upper and lower lip mucocutaneous border. A fraction of the toxin penetrates the cutaneous layer and exerts a therapeutic effect. The gauze remains in place for 30 minutes and is then discarded. The woman experiences a slight to moderate numbness in her lips, making it very difficult and displeasing to hold a cigarette between her lips. This alteration in sensation and negative association breaks her of her smoking addiction. Within 1-7 days the patient has less of an urge to smoke, leading to her long term cessation of smoking.

Example 8

Topical Application

A 30 year old man presents to his physician with an addiction to cocaine. The physician applies 50 units of botulinum toxin type A by soaking gauze on the skin around the nostrils, or on the skin within the nostrils, or on the nasal mucosa (including septum, turbinates or sinus mucosa). The gauze remains in place for 30 minutes and is then discarded. The man experiences a slight to moderate numbness in nose, making it very difficult and displeasing to take in any substance through his nose. These alterations in sensation and negative associations break him of his sniffing addiction. Within 1-7 days the patient has less of an urge to sniff cocaine, leading to his long term cessation of the addiction.

Having thus described in detail embodiments of the present invention, it is to be understood that the invention defined by the above paragraphs is not to be limited to particular details set forth in the above description as many apparent variations thereof are possible without departing from the spirit or scope of the present invention.

Each patent, patent application, and publication cited or described in the present application is hereby incorporated by reference in its entirety as if each individual patent, patent application, or publication was specifically and individually indicated to be incorporated by reference.

What is claimed is:

1. A method of treating a substance addiction-related behavior in a patient, comprising
   administering by a non-systemic route a therapeutically effective dose of a botulinum neurotoxin to a location on the patient's body which comes into contact with a smoking tool or addictive substance,
   wherein the location is selected from the group consisting of: thumb, index finger, middle finger and a combination thereof, thereby altering peripheral sensation of the body location,
   wherein said therapeutically effective dose is sufficient to inhibit a sensory output from a muscle to the central nervous system such that generation of a premonitory urge or motor output associated with the substance addiction-related behavior in the body location is reduced but is less than a dose necessary to produce a substantial muscle weakness within the affected location.

2. The method of claim: 1, further comprising administering a therapeutically effective dose of a botulinum neurotoxin to an additional body location that comes in contact with a smoking tool or addictive substance inside of or around the opening of the mouth or nasal cavity of the patient or to a location on the hand or hands of the patient, thereby altering peripheral sensation of the body area.

3. The method of claim 2, wherein the body location inside of the patient's mouth is the mucosal lining or salivary gland.

4. The method of claim 3, wherein said therapeutically effective dose is sufficient to reduce mucosal/salivary secretions of the mouth, thereby having a drying effect on the mouth.

5. The method of claim 2, wherein the body location around the opening of the patient's mouth is the lips or area immediately surrounding the lips.

6. The method of claim 5, wherein the body location is within an about 1 $cm^2$ area surrounding the patient's lips.

7. The method of claim 2, wherein the body location is on a patient's hand or hands.

8. The method of claim 2, wherein administration of the botulinum neurotoxin is to a dermal, subdermal, mucosal, or submucosal location or to a muscle that a smoking tool or addictive substance contacts.

9. The method of claim 8, wherein administration to the dermal location is by transdermal or transmucosal delivery.

10. The method of claim 9, wherein the transdermal or transmucosal delivery is via a patch, cream, ointment or lotion vehicle comprising botulinum neurotoxin.

11. The method of claim 8, wherein administration to the muscle is by intramuscular injection.

12. The method of claim 2 or 4, wherein the alteration in sensation or mucosal/salivary secretion persists for between about 1 month and about 6 months.

13. The method of claim 1, wherein the smoking tool is selected from the group consisting of: a cigarette, a cigar, a pipe, a hookah, a bong and any tool from which tobacco, marijuana, cocaine and any addictive substance may be smoked.

14. The method of claim 1, wherein the botulinum neurotoxin is selected from the group consisting of botulinum neurotoxin serotype A, B, $C_1$, D, E, F and G.

15. The method of claim 14, wherein the botulinum neurotoxin is botulinum neurotoxin serotype A.

16. The method of claim 14, wherein the botulinum neurotoxin is botulinum neurotoxin serotype B.

17. The method of claim 15, wherein the botulinum neurotoxin is topically administered in an amount of between about 0.25 units and about 1,500 units of serotype A toxin.

18. The method of claim 16, wherein the botulinum neurotoxin is administered in an amount of between about 1 unit and about 50,000 units.

19. A method of treating a substance addiction-related behavior in a patient, comprising
   administering by a non-systemic route a therapeutically effective dose of a botulinum neurotoxin to the nasal cavity of the patient's body which comes into contact with a smoking tool or addictive substance thereby altering peripheral sensation of the body location,
   wherein said therapeutically effective dose is sufficient to inhibit a sensory output from a muscle to the central nervous system such that generation of a premonitory urge or motor output associated with the substance addiction-related behavior in the body location is reduced but is less than a dose necessary to produce a substantial muscle weakness within the affected location.

\* \* \* \* \*